United States Patent
Urano et al.

(10) Patent No.: US 12,420,012 B2
(45) Date of Patent: Sep. 23, 2025

(54) INFUSION SET

(71) Applicant: COMETS INC., Tokyo (JP)

(72) Inventors: Masahito Urano, Yokohama (JP); Seiji Yonezawa, Tokyo (JP)

(73) Assignee: COMETS INC., Tokyo (JP)

(*) Notice: Subject to any disclaimer, the term of this patent is extended or adjusted under 35 U.S.C. 154(b) by 518 days.

(21) Appl. No.: 17/937,993

(22) Filed: Oct. 4, 2022

(65) Prior Publication Data

US 2023/0027948 A1 Jan. 26, 2023

Related U.S. Application Data

(62) Division of application No. 16/900,792, filed on Jun. 12, 2020, now Pat. No. 11,701,466.

(30) Foreign Application Priority Data

Jan. 15, 2020 (JP) ................. 2020-004576

(51) Int. Cl.
  *A61M 5/168* (2006.01)
  *A61M 5/14* (2006.01)
  *A61M 39/28* (2006.01)

(52) U.S. Cl.
  CPC ...... *A61M 5/16813* (2013.01); *A61M 5/1411* (2013.01); *A61M 5/16827* (2013.01); *A61M 39/28* (2013.01); *A61M 5/1407* (2013.01)

(58) Field of Classification Search
  CPC .............. A61M 5/1407; A61M 5/1411; A61M 5/16813; A61M 5/16827; A61M 39/1407; A61M 39/28
  See application file for complete search history.

(56) References Cited

U.S. PATENT DOCUMENTS

| 2,586,513 | A | * | 2/1952 | Butler | .................. | A61M 5/165 |
| | | | | | | 210/94 |
| 3,954,623 | A | * | 5/1976 | Hammer | .............. | B01D 36/001 |
| | | | | | | 215/261 |
| 3,978,857 | A | * | 9/1976 | McPhee | ................ | A61M 5/165 |
| | | | | | | 604/257 |

(Continued)

FOREIGN PATENT DOCUMENTS

| BE | 893949 A | 11/1982 |
| CN | 202554599 U | 11/2012 |

(Continued)

*Primary Examiner* — Bhisma Mehta
*Assistant Examiner* — Mark A Igel
(74) *Attorney, Agent, or Firm* — Studebaker Brackett PLLC

(57) ABSTRACT

There is provided an infusion set capable of significantly reducing a period of time required for work of a worker during infusion. The infusion set includes a drip chamber, a tube which is connected to an outlet of the drip chamber, a roller clip which is provided in the tube, and an M clamp which is provided between the drip chamber and the roller clip in the tube and is used for storing liquid in the drip chamber. The tube has a first tube which can be mounted to an infusion pump device, a second tube which is connected to the outlet of the drip chamber and an inlet of the first tube, and a third tube which is connected to an outlet of the first tube. The M clamp is provided in the second tube, and the roller clip is provided in the third tube.

5 Claims, 10 Drawing Sheets

(56) References Cited

U.S. PATENT DOCUMENTS

| | | | | |
|---|---|---|---|---|
| 4,009,714 A * | 3/1977 | Hammer | A61M 5/165 | |
| | | | 604/126 | |
| 4,035,304 A * | 7/1977 | Watanabe | A61M 5/165 | |
| | | | 210/317 | |
| 4,073,732 A * | 2/1978 | Lauer | B32B 5/022 | |
| | | | 55/487 | |
| 4,080,113 A * | 3/1978 | Legeay, nee Lechat | | |
| | | | F04B 43/0072 | |
| | | | 138/118 | |
| 4,087,363 A * | 5/1978 | Rosemeyer | A61M 5/165 | |
| | | | 210/489 | |
| 4,116,845 A * | 9/1978 | Swank | A61M 5/165 | |
| | | | 210/451 | |
| 4,126,558 A * | 11/1978 | Luceyk | A61M 5/165 | |
| | | | 210/429 | |
| 4,276,170 A * | 6/1981 | Vaillancourt | B01D 36/001 | |
| | | | 96/6 | |
| 4,303,530 A * | 12/1981 | Shah | A61M 1/3627 | |
| | | | 210/651 | |
| 4,432,754 A * | 2/1984 | Urquhart | A61M 5/1407 | |
| | | | 604/80 | |
| 4,432,756 A * | 2/1984 | Urquhart | A61M 5/1407 | |
| | | | 604/80 | |
| 4,450,078 A * | 5/1984 | Walker | A61M 5/165 | |
| | | | 210/489 | |
| 4,451,255 A * | 5/1984 | Bujan | A61M 5/16827 | |
| | | | 604/153 | |
| 4,479,874 A * | 10/1984 | Rosenberg | B01D 29/012 | |
| | | | 210/446 | |
| 4,517,090 A * | 5/1985 | Kersten | B01D 29/232 | |
| | | | 264/250 | |
| 4,547,190 A * | 10/1985 | Leason | A61M 5/165 | |
| | | | 604/185 | |
| 4,963,262 A * | 10/1990 | Johnstone | A47J 31/06 | |
| | | | 210/477 | |
| 4,978,446 A * | 12/1990 | Lobdell | A61M 1/0218 | |
| | | | 604/408 | |
| 5,088,522 A * | 2/1992 | Rath | F04B 43/0072 | |
| | | | 138/119 | |
| 5,207,642 A * | 5/1993 | Orkin | A61M 5/16827 | |
| | | | 604/905 | |
| 5,242,279 A * | 9/1993 | Knuth | A61M 39/08 | |
| | | | 417/474 | |
| 5,968,014 A * | 10/1999 | Neftel | A61M 5/007 | |
| | | | 604/151 | |
| 7,162,290 B1 * | 1/2007 | Levin | A61B 5/68 | |
| | | | 600/385 | |
| 10,563,646 B2 * | 2/2020 | Galavotti | F04B 43/0072 | |
| 2002/0033370 A1 * | 3/2002 | Bainbridge | A61M 1/303 | |
| | | | 604/6.11 | |
| 2004/0059287 A1 * | 3/2004 | Vest | A61M 5/14 | |
| | | | 604/80 | |
| 2009/0018513 A1 * | 1/2009 | Fujii | F16K 15/148 | |
| | | | 604/247 | |
| 2015/0018765 A1 * | 1/2015 | Wong | A61M 5/1411 | |
| | | | 604/126 | |
| 2020/0268966 A1 * | 8/2020 | Längle | A61M 5/16877 | |

FOREIGN PATENT DOCUMENTS

| | | |
|---|---|---|
| GB | 2030466 A | 4/1980 |
| JP | H08-084770 A | 4/1996 |
| JP | 2016-059535 A | 4/2016 |
| JP | 2017-501753 A | 1/2017 |
| JP | 2018027193 A * | 2/2018 |
| JP | 2018-164530 A | 10/2018 |
| JP | 2018-533459 A | 11/2018 |
| WO | 2007/083599 A1 | 7/2007 |
| WO | 2016/093890 A1 | 6/2016 |
| WO | 2017/085605 A1 | 5/2017 |

* cited by examiner

INFUSION SET

CROSS-REFERENCE TO RELATED APPLICATIONS

This application is a Divisional of U.S. patent application Ser. No. 16/900,792 filed Jun. 12, 2020, which claims benefit of priority to Japanese Patent Application No. 2020-004576 filed Jan. 15, 2020, the entire contents of which are incorporated herein by reference.

BACKGROUND

Field

The present invention relates to an infusion set.

Description of Related Art

There is an infusion set which is used during infusion such as blood transfusion. As shown in FIG. 8, the infusion set typically incudes a drip chamber 200, an upstream tube 202 which is connected to a blood bag 201 and the drip chamber 200, an upstream tube 204 which is connected to a saline bag 203 and the drip chamber 200, a tube 206 which is connected to an outlet of the drip chamber 200, a roller clip 207 which is provided in the tube 206 and can adjust the flow speed of an infusion solution, and clamps 208 and 209 which are provided in the upstream tubes 202 and 204, respectively. To the tip of the tube 206, a tip connector 210 which can be connected to an indwelling needle which is already inserted into a patient is attached.

When infusion is performed using the infusion set, as preliminary work for infusion, as shown in FIG. 9, a nurse first opens the clamp 209, and presses the drip chamber 200 to introduce saline A in the saline bag 203 into the drip chamber 200 through the upstream tube 204. Next, the nurse opens the roller clip 207, and supplies the saline A in the drip chamber 200 to the tip connector 210 of the tube 206 from the drip chamber 200. This is because it is necessary to remove gas in in the tube 206 in advance to prevent bubbles from being mixed into the body of the patient and, when blood is supplied to the drip chamber 200 first, a filter 211 of the drip chamber 200 may be clogged, and hence it is necessary to introduce the saline A to the filter 211 of the drip chamber 200 in advance to dilute blood.

When infusion is started, as shown in FIG. 10, the nurse opens the clamp 208 after closing the clamp 209 to introduce blood B in the blood bag 201 into the drip chamber 200, and the saline A and diluted blood B' are thereby introduced into the drip chamber 200. Subsequently, the nurse sets the tube 206 in a pump device 212, and connects the tip connector 210 of the tube 206 to the indwelling needle which is already inserted into the patient. The nurse then operates the pump device 212 to cause blood in the blood bag 201 to flow to the tip connector 210 of the tube 206 from the drip chamber 200 and supply the blood to the patient.

SUMMARY

However, as shown in FIG. 10, when infusion is started, the saline A filled in the tube 206 is supplied to the patient first, the blood B' diluted with the saline in the drip chamber 200 or the like is supplied to the patient next, and the pure blood B which does not contain the saline is supplied to the patient thereafter. At this point, it takes about 15 minutes before all of the saline A in the tube 206 is introduced into the body of the patient and the supply of the pure blood B into the body of the patient is started.

The nurse needs to see whether or not the patient shows rejection for about 15 minutes from the start of supply of the pure blood B to the patient in order to determine whether or not the blood serving as the infusion solution is compatible with the patient. Therefore, the nurse needs to continuously observe the state of the infusion in a sickroom for about 15 minutes from the start of introduction of the pure blood B into the patient in addition to about 15 minutes from when the infusion is started until when all of the saline A in the entire tube 206 is introduced into the patient and the introduction of the diluted blood B' in the drip chamber 200 into the patient is ended.

Thus, in the infusion which uses the conventional infusion set, a long period of time is required from when the preliminary work for the infusion is started until when it is determined whether or not the rejection of the patient is present, working time of the nurse is long, and the burden of the nurse is increased.

The present invention is achieved in view of such points, and an object thereof is to provide an infusion set capable of significantly reducing a period of time required for work of a worker such as a nurse during infusion.

An infusion set according to an aspect of the present invention includes: a drip chamber; a tube which is connected to an outlet of the drip chamber; a flow rate adjustment part which is provided in the tube; and a clamp which is provided between the drip chamber and the flow rate adjustment part in the tube and is used for storing liquid in the drip chamber.

According to the present aspect, it is possible to significantly reduce a period of time required for work of a worker during infusion.

The tube may have a section which can be mounted to an infusion pump device, the flow rate adjustment part may be provided in the section or downstream of the section, and the clamp may be provided upstream of the section.

The tube may have: a first tube which can be mounted to the infusion pump device; a second tube which is connected to the outlet of the drip chamber and an inlet of the first tube; and a third tube which is connected to an outlet of the first tube, the clamp may be provided in the second tube, and the flow rate adjustment part may be provided in the third tube.

The clamp may be provided at a position within 100 cm from the outlet of the drip chamber in the tube.

The clamp may be movable along the tube.

The infusion set may further include a clamp which is provided between the flow rate adjustment part and the clamp in the tube and prevents a free flow.

The infusion set may further include: an upstream tube which is connected to an inlet of the drip chamber and can be connected to a liquid bag; and a clamp which is provided in the upstream tube.

According to the present invention, it is possible to significantly reduce a period of time required for work of a worker during infusion.

DETAILED DESCRIPTION

Figure 1:
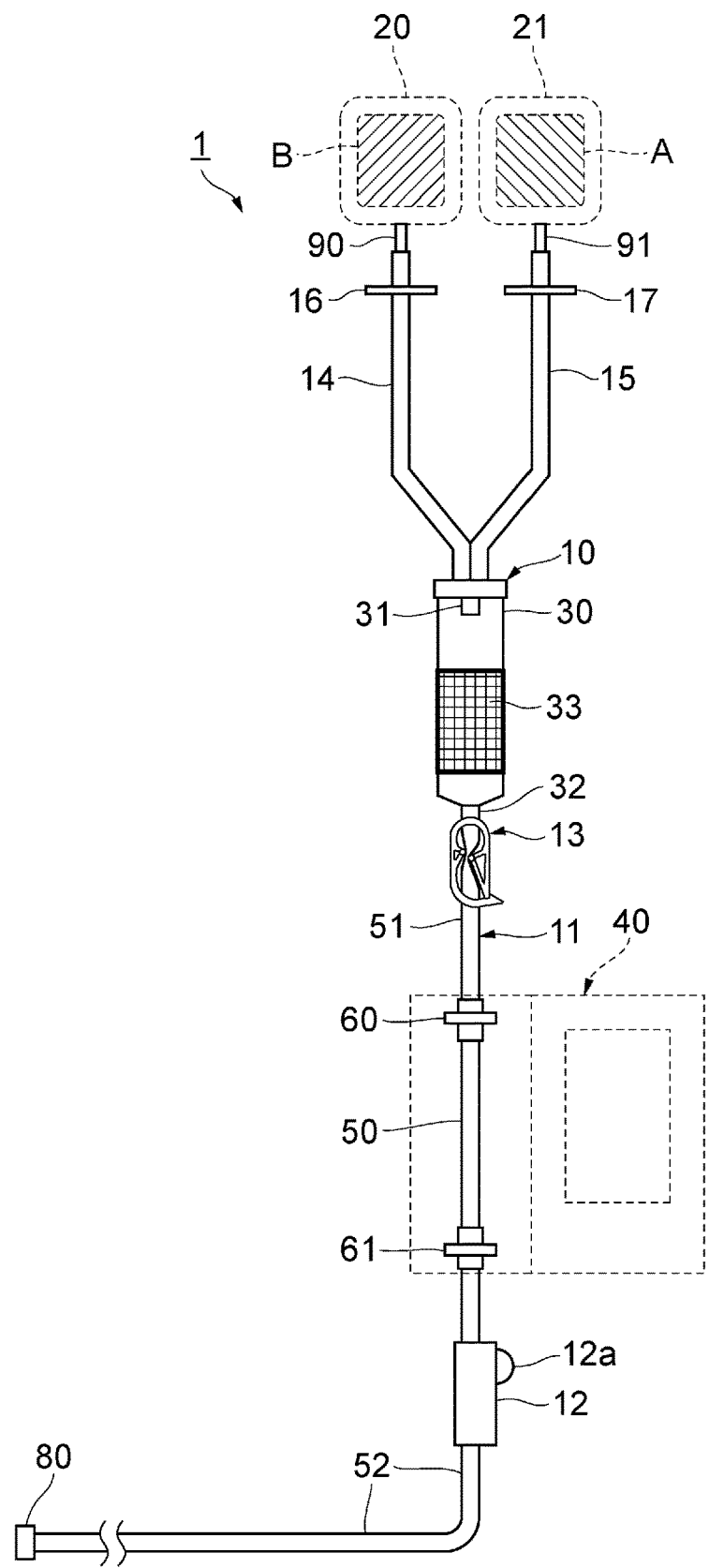
FIG. 1 is a schematic view showing an example of the structure of an infusion set of the present embodiment.

Hereinbelow, with reference to the drawings, preferred embodiments of the present invention will be described. Note that the same elements are designated by the same reference numerals, and the duplicate description thereof will be omitted. In addition, dimensional ratios in the drawings are not limited to those shown in the drawings. Further, the following embodiments are shown by way of example only for explaining the present invention, and the present invention is not limited to the embodiments.

FIG. 1 is an explanatory view showing an example of the structure of an infusion set 1 according to the present embodiment. The infusion set 1 includes, e.g., a drip chamber 10, a tube 11 which is connected to an outlet of the drip chamber 10, a roller clip 12 which is provided in the tube 11 and serves as a flow rate adjustment part, an M clamp 13 which is provided between the drip chamber 10 and the roller clip 12 in the tube 11, a first upstream tube 14 which is connected to an inlet of the drip chamber 10 and can be connected to a first bag 20, a second upstream tube 15 which is connected to the inlet of the drip chamber 10 and can be connected to a second bag 21, a first clamp 16 which is provided in the first upstream tube 14, and a second clamp 17 which is provided in the second upstream tube 15.

The drip chamber 10 has a cylindrical main body 30, has a dripping part 31 in an upper portion of the main body 30, and has an outlet part 32 in a lower portion of the main body 30. The main body 30 is formed of soft resin, and is structured to replace gas with liquid by being pressed with a hand. In addition, the drip chamber 10 has a filter 33 for filtering out impurities inside the main body 30. The drip chamber 10 is structured such that s droplet is dripped from the dripping part 31, is stored in the main body 30 through the filter 33, and is discharged from the outlet part 32.

The tube 11 has a first tube 50 which can be mounted to, e.g., an infusion pump device 40, a second tube 51 which is connected to the outlet of the drip chamber 10 and an inlet of the first tube 50, and a third tube 52 which is connected to an outlet of the first tube 50.

For example, the first tube 50 is extended and mounted in the infusion pump device 40, and hence the first tube 50 is softer than the second tube 51 and the third tube 52. For example, the first tube 50 has connectors 60 and 61 at both ends of the first tube 50. The first connector 60 on the upstream side connects the first tube 50 and the second tube 51. The second connector 61 on the downstream side connects the first tube 50 and the third tube 52. Note that it is possible to integrate the first tube 50, the second tube 51, and the third tube 52 into one tube by using the material of the first tube 50 as the material of each of the second tube 51 and the third tube 52.

For example, each of the first connector 60 and the second connector 61 has a mounting function for fitting the first tube 50 in the infusion pump device 40 to mount the first tube 50 to the infusion pump device 40. The second connector 61 includes a function as a clamp for opening and closing the first tube 50 in the case of a malfunction such as opening of an operation panel of the infusion pump device 40. For example, the second connector 61 is structured to open the first tube 50 when the first tube 50 is mounted to the infusion pump device 40. Note that the infusion pump device 40 may be provided with, e.g., a lid which is opened and closed when the first tube 50 is mounted and, at this point, the second connector 61 may include, e.g., a free flow prevention function which closes the first tube 50 when the lid of the infusion pump device 40 is opened. That is, in this case, the second connector 61 functions as a clamp for preventing the free flow which can be attached to the infusion pump device 40.

The third tube 52 has a tip connector 80 at an end portion on its outlet side. The tip connector 80 can be connected to a connector of an indwelling needle attached to a patient side, or a connection tube connected to the connector of the indwelling needle.

The roller clip 12 is provided in the third tube 52. The roller clip 12 is allowed to change the degree of opening of the third tube 52 to adjust the flow speed of liquid flowing in the tube 11 by manually turning a roller 12a. Note that the roller clip 12 is movable along the third tube 52 but cannot move to the first tube 50.

Figure 2:
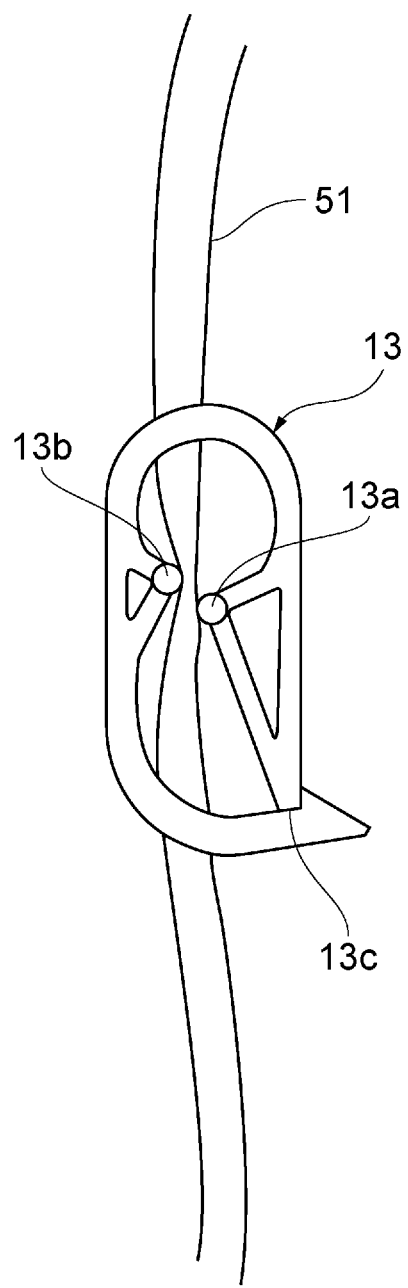
FIG. 2 is an explanatory view showing an M clamp.

The M clamp 13 is provided in the second tube 51. The M clamp 13 has a function of opening and closing the second tube 51. The M clamp 13 can be used for storing saline and blood in the drip chamber 10 at the same time. The M clamp 13 is provided, e.g., at a position within 100 cm from the outlet of the drip chamber 10 in the second tube 51, more preferably at a position within 10 cm therefrom, even more preferably at a position within 5 cm therefrom, and still even more preferably at a position immediately below the drip chamber 10. The M clamp 13 may be appropriately provided in the vicinity of the outlet of the drip chamber 10, i.e., within 3 cm from the outlet of the drip chamber 10. As shown in FIG. 2, the M clamp 13 has a substantially oval annular shape. The M clamp 13 has clamping parts 13a and 13b which face each other with the second tube 51 interposed therebetween, and a holding part 13c. The M clamp 13 is allowed to close the second tube 51 by pressing the clamping parts 13a and 13b in a direction in which the clamping parts 13a and 13b approach each other, and can hold its closed state with the holding part 13c. In addition, disconnection of the holding part 13c allows the clamping parts 13a and 13b to be moved away from each other, and the M clamp 13 can open the second tube 51. The M clamp 13 is movable along the tube 11. The M clamp 13 may also be fixed to a predetermined position of the tube 11. The M clamp 13 may be detachable from the tube 11. In addition, the M clamp 13 is the clamp of a type different from those of the clamps 16 and 17.

The first upstream tube 14 has a connection part 90 which is used for insertion into and connection to the first bag 20 at an end portion on its upstream side. Similarly, the second upstream tube 15 has a connection part 91 which is used for insertion into and connection to the second bag 21 at an end portion on its upstream side. In the present embodiment, the first bag 20 is a blood bag in which blood B is stored, and the second bag 21 is a saline bag in which saline A is stored. Note that the second bag 21 is not limited to the saline bag, and may also be a drug solution bag in which a drug solution other than the saline is stored.

The first clamp 16 and the second clamp 17 have functions of manually opening and closing the first upstream tube 14 and the second upstream tube 15, respectively.

The infusion pump device 40 automatically controls the flow speed of the infusion solution with programming, and can connect to, e.g., the first tube 50 and send blood in the drip chamber 10 to the tip connector 80 at a predetermined set flow speed.

Next, a description will be given of a process of infusion which is performed by using the infusion set 1 structured as described above. Before the first bag 20 (blood) is released from a blood bank, a worker serving as a nurse first closes the clamp 17, the M clamp 13, and the roller clip 12 of the infusion set 1 shown in FIG. 1 to close all tubes. At this point, the M clamp 13 closes the second tube 51 in the vicinity of an upper end of the second tube 51, i.e., at a position immediately below the drip chamber 10 (a connection portion between the drip chamber 10 and the second tube 51).

Figure 3:
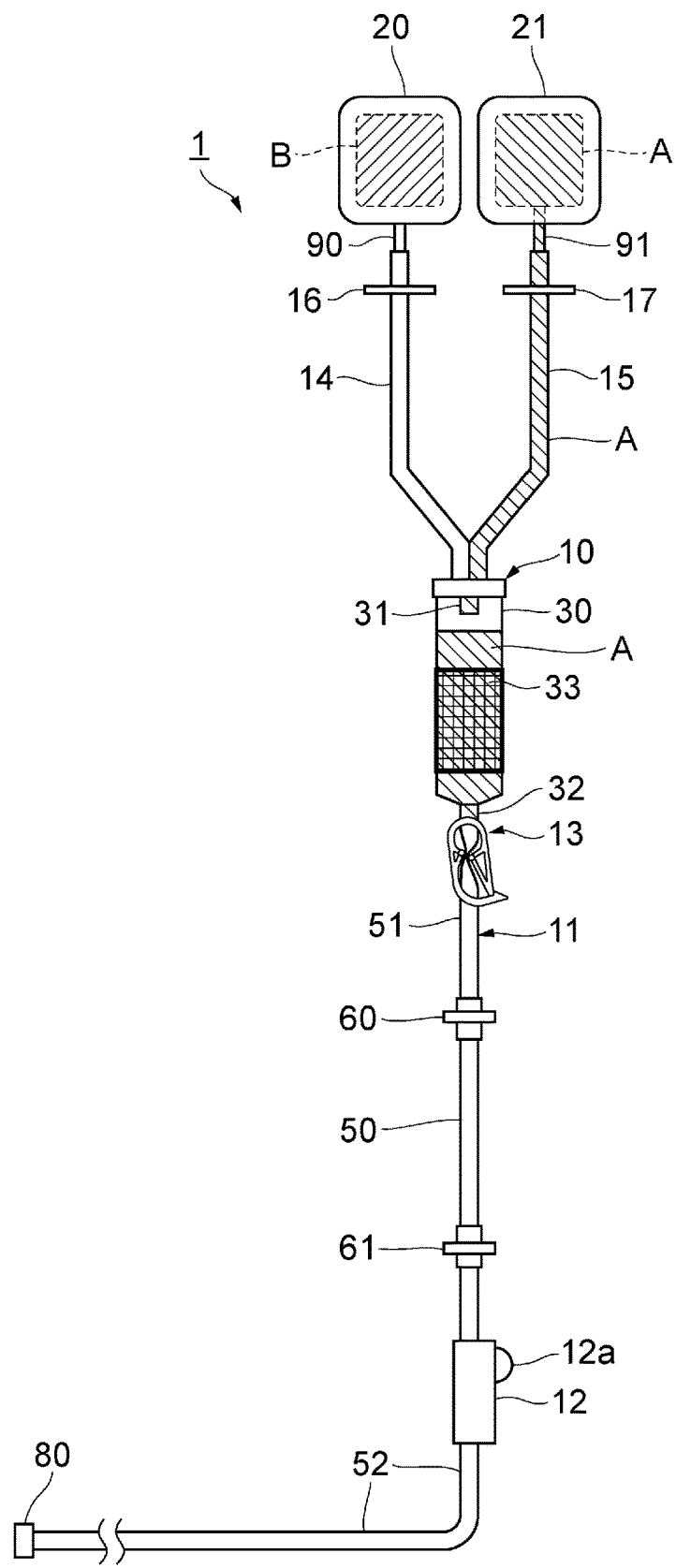
FIG. 3 is an explanatory view showing a state in which saline is put in a drip chamber of the infusion set of the present embodiment.

Next, the worker connects the connection part 91 of the second upstream tube 15 to the second bag 21 serving as, e.g., the saline bag, and hangs the second bag 21 from a stand for infusion (not shown). By opening the second clamp 17 to open the second upstream tube 15 and pressing the main body 30 of the drip chamber 10 to increase and decrease the internal capacity of the main body 30, the worker causes the saline A in the second bag 21 to flow into the drip chamber 10, as shown in FIG. 3. At this point, the second tube 51 is closed at the position immediately below the drip chamber 10 by the M clamp 13, and the saline A is prevented from flowing into the first tube 50 and the third tube 52 via the second tube 51. When the saline A is stored in the drip chamber 10 and the saline A penetrates into the filter 33, the worker closes the second clamp 17 to close the second upstream tube 15.

After checking documents such as a written approval for blood transfusion, the worker contacts the blood bank after determining that there is no abnormality by measuring blood pressure, respiratory rate, heart rate, and body temperature, and the blood bag is then released. After receiving the blood bag safely, the worker checks the patient name, patient number, blood type, and documents, and then connects the connection part 90 of the first upstream tube 14 to the first bag 20 serving as the blood bag, and hangs the first bag 20 from the stand for infusion.

Figure 4:
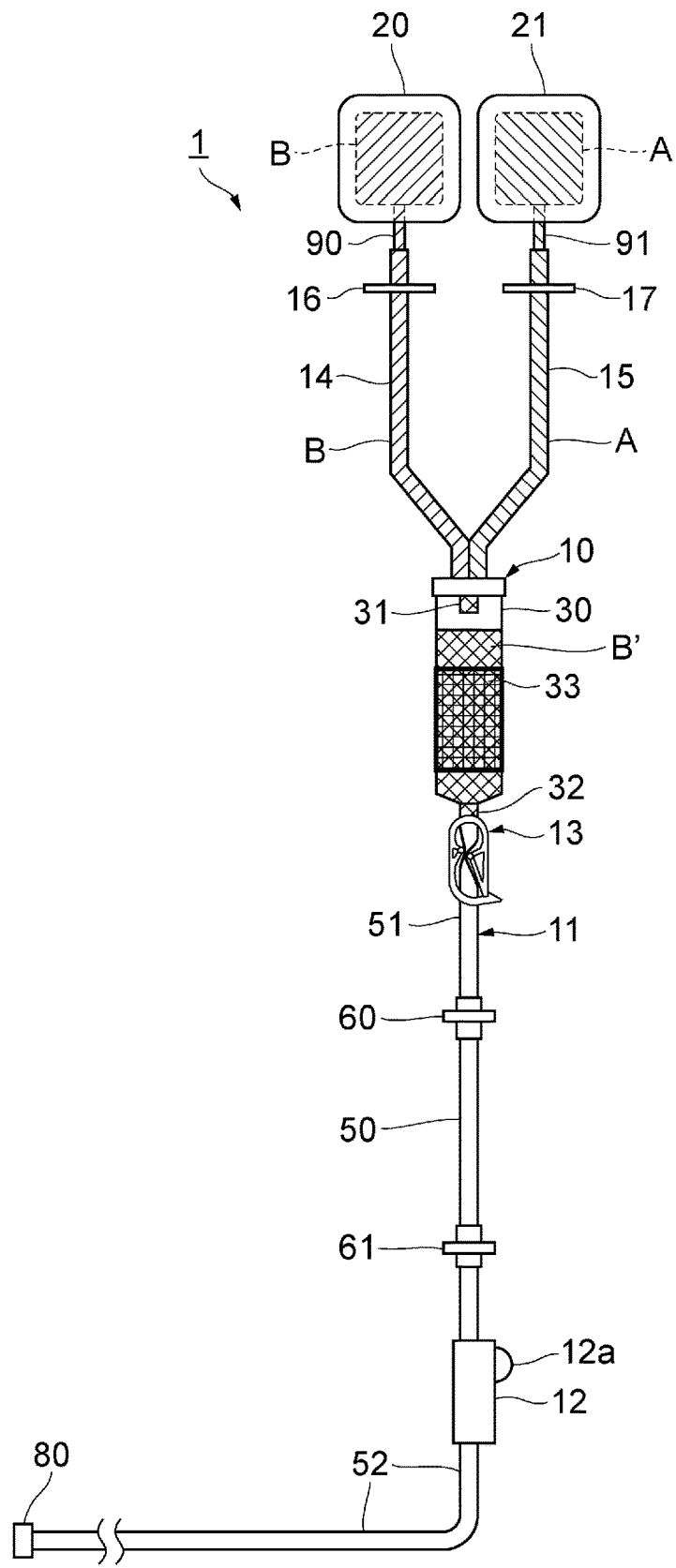
FIG. 4 is an explanatory view showing a state in which blood is supplied to the drip chamber of the infusion set of the present embodiment and the blood is diluted with the saline.

Next, the worker opens the first clamp 16 to open the first upstream tube 14, presses the main body 30 of the drip chamber 10, and causes the blood B in the first bag 20 to flow into the drip chamber 10, as shown in FIG. 4. At this point, the blood B having entered the drip chamber 10 is mixed with the saline A which has been in the drip chamber 10, and becomes blood B' which is diluted with the saline A. In addition, the second tube 51 is closed at the position immediately below the drip chamber 10 by the M clamp 13, and hence the blood B' stays in the drip chamber 10.

Figure 5:
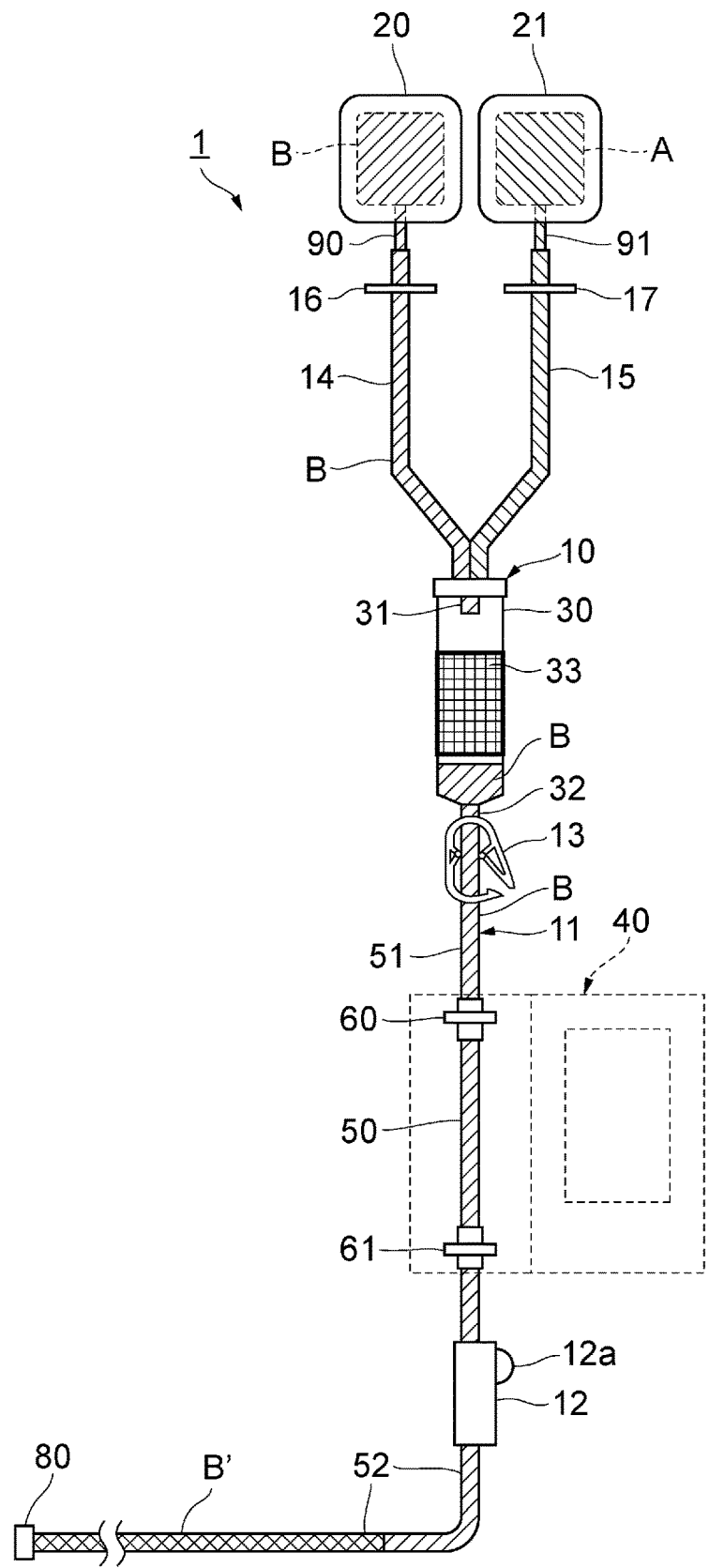
FIG. 5 is an explanatory view showing a state in which gas in a tube is removed in the infusion set of the present embodiment.

Subsequently, in a state in which the second clamp 17 is closed and the first clamp 16 is open, the worker opens the M clamp 13 to open the second tube 51, and opens the roller clip 12 to open the third tube 52. With this, as shown in FIG. 5, the blood B' in the drip chamber 10 passes through the second tube 51, the first tube 50, and the third tube 52 in this order, reaches the tip connector 80, washes away all gas in the tube 11, and the gas is removed. Since the tube 11 is not provided in the infusion pump device 40, the gas is released into the air and resistance is low in the work for gas removal, and hence the work for gas removal is completed in a short period of time.

Figure 6:
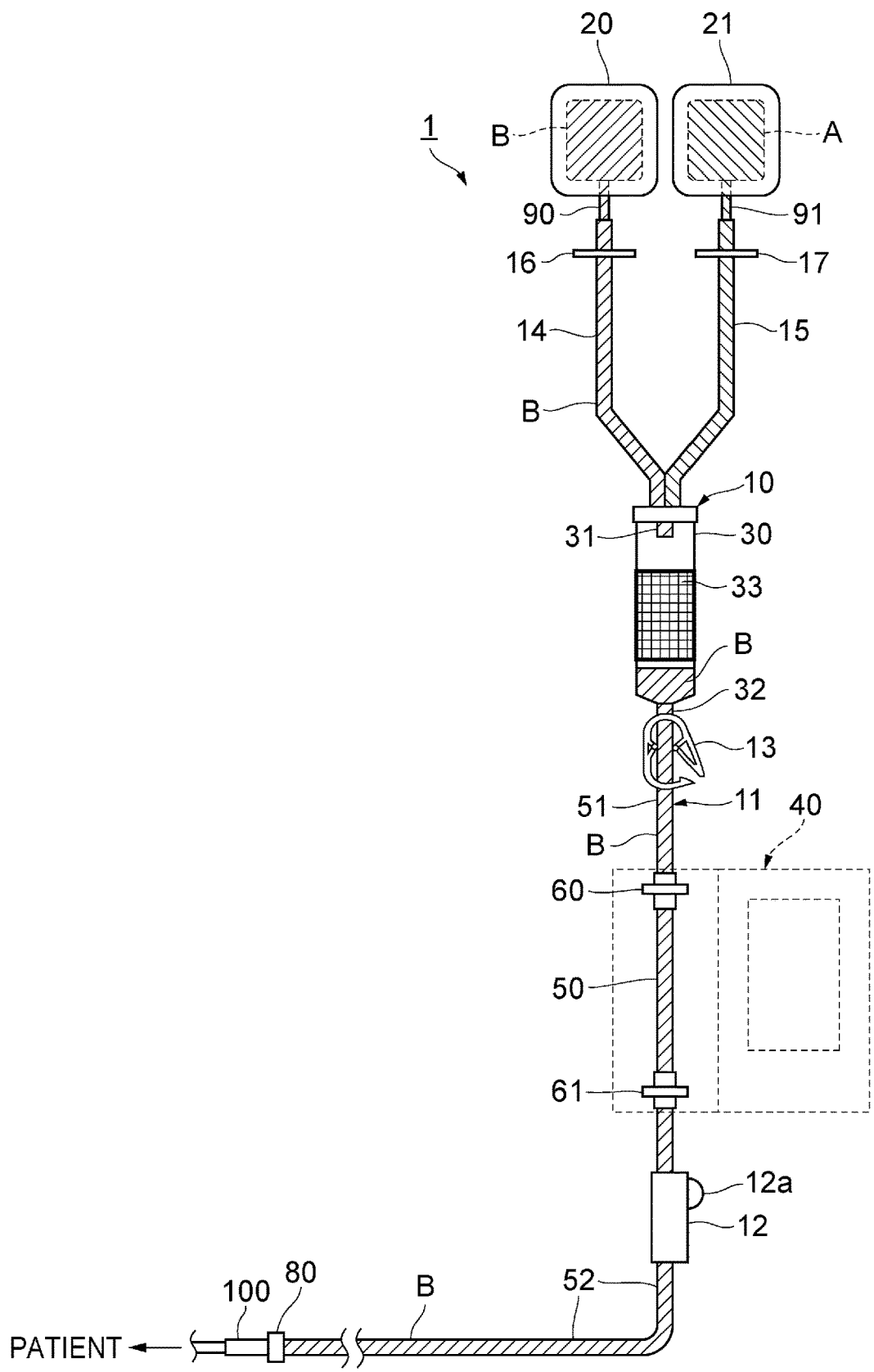
FIG. 6 is an explanatory view showing a state when infusion of the infusion set of the present embodiment is performed.

Subsequently, the worker attaches the first tube 50 to the infusion pump device 40. At this point, the first connector 60 and the second connector 61 of the first tube 50 are fitted in predetermined portions of the infusion pump device 40, and the first tube 50 is thereby fixed to the infusion pump device 40. Next, the worker performs programming of settings such as infusion speed or the like (e.g., 100 mL/hour) in the infusion pump device 40, and connects the tip connector 80 of the tube 11 to the connector 100 on the patient side, as shown in FIG. 6. The worker operates the infusion pump device 40 to start the infusion of blood to the patient. At this point, while blood mixed with a very small amount of saline is supplied to the patient, it is possible to quickly determine the presence or absence of rejection and side effects.

Figure 9:
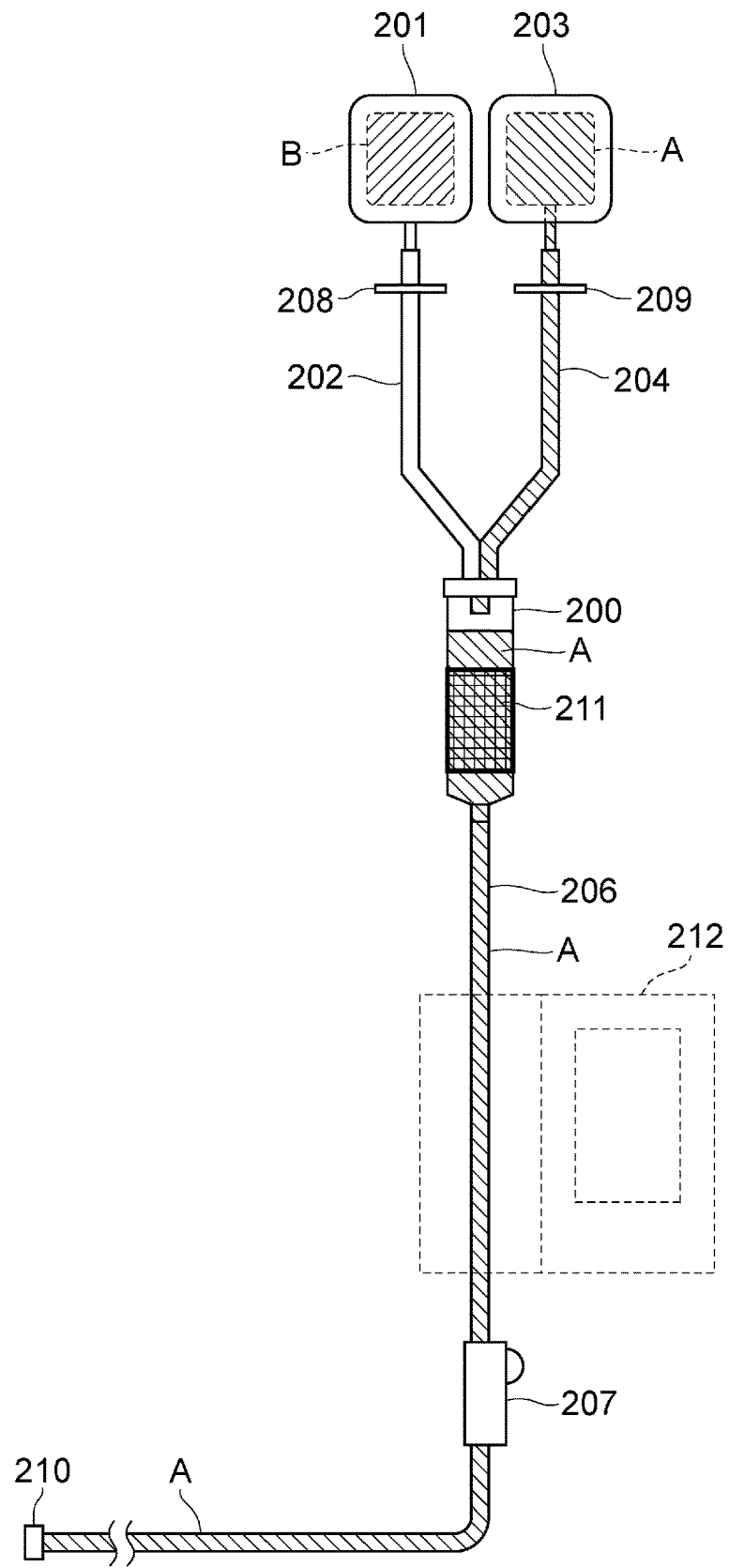
FIG. 9 is an explanatory view showing a state in which a tube of the conventional infusion set is filled with saline.
Figure 10:
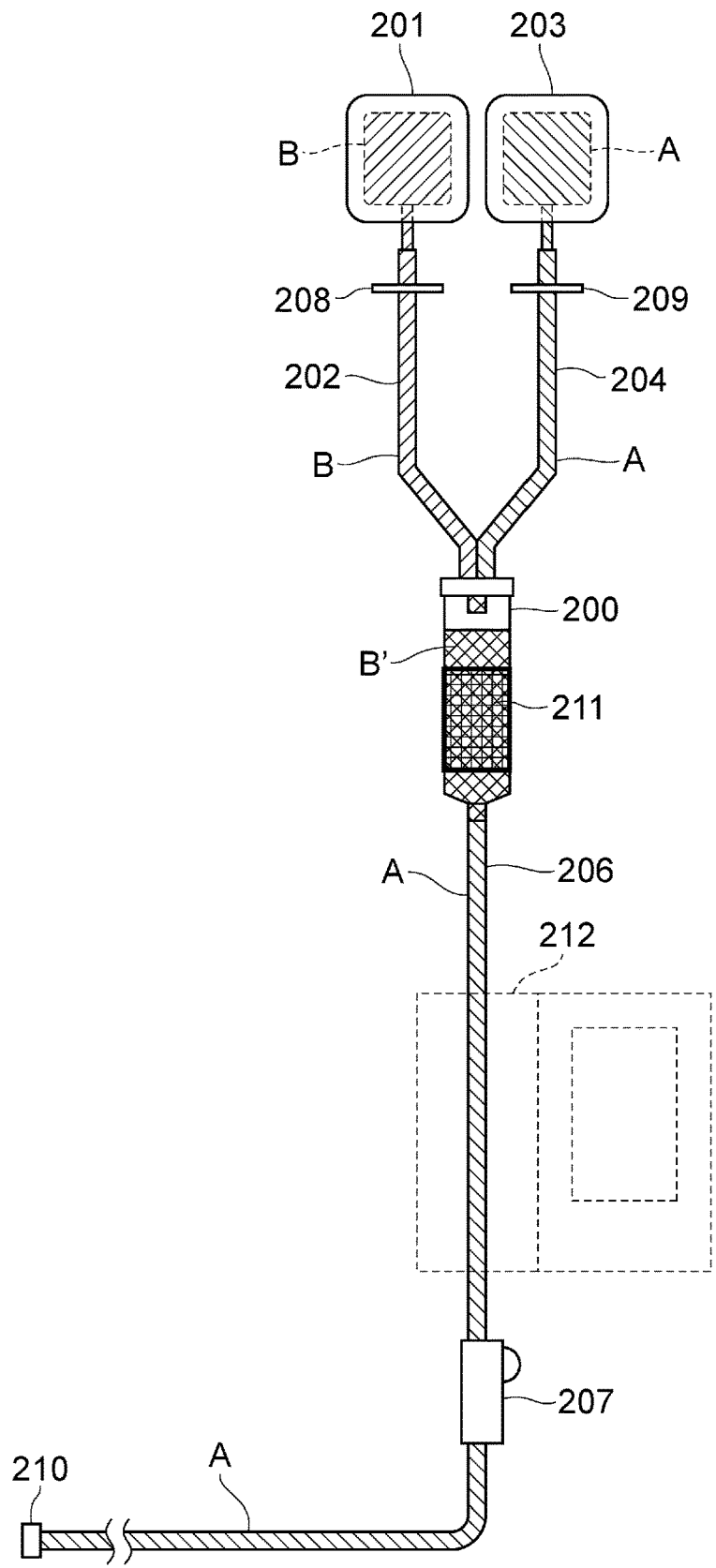
FIG. 10 is an explanatory view showing a state in which blood is supplied to a drip chamber of the conventional infusion set.

According to the present embodiment, the infusion set 1 includes the drip chamber 10, the tube 11 which is connected to the outlet of the drip chamber 10, the roller clip 12 which is provided in the tube 11, and the M clamp 13 which is provided between the drip chamber 10 and the roller clip 12 in the tube 11. With this, as shown in FIG. 3, it is possible to cause the saline A to enter the drip chamber 10 in the state in which the tube 11 is closed by the M clamp 13 provided between the drip chamber 10 and the roller clip 12, and hence it is not necessary to fill the entire tube 11 positioned downstream of the drip chamber 10 with the saline A. Consequently, work for filling an entire tube 206 with saline A, which is performed in a conventional infusion set shown in FIG. 9, is eliminated. When infusion is started, the blood B' diluted with the saline A shown in FIG. 5 and the pure blood B are supplied to the patient in this order, and supply of blood after the saline A filled in the tube 206 is supplied to the patient, which is performed in the conventional infusion set shown in FIG. 10, is not performed. Consequently, it is possible to reduce a period of time from when the infusion is started until when the supply of the pure blood B to the patient is started, and reduce a period of time required to complete the determination of whether or not the rejection of the patient is present. As a result, it is possible to significantly reduce a period of time required for the work of the worker during infusion to thereby reduce actual working hours of the worker and reduce the burden of the worker.

In addition, according to the present embodiment, unlike the conventional infusion set, it is not necessary to fill the entire tube with the saline A, and hence it is possible to reduce the amount of consumption of the saline A.

The M clamp 13 is provided at the position, e.g., immediately below the drip chamber 10 within 10 cm from the outlet of the drip chamber 10 in the tube 11, and hence the amount of the blood B' diluted with the saline A is small, and timing at which the supply of the pure blood B to the patient is started can be made earlier. Therefore, it is possible to reduce a period of time required for the work of the worker during infusion. In addition, it is possible to remove the gas by using the blood B', and hence it is possible to connect the tube 11 to the connector 100 on the patient side immediately after the removal to introduce the blood B into the patient. As a result, it is possible to prevent an unsanitary and improper act in which, in order to quickly remove the saline in the tube and the diluted solution of the blood diluted with the saline, the saline in the tube and the diluted solution are dumped in a trash box in advance.

While the tube 11 has the first tube 50, the second tube 51, and the third tube 52 in the above embodiment, the tube 11 may be formed of one continuous tube, and may not be constituted by a plurality of tubes. In this case, in the tube 11, a clamp with a free flow prevention function may be provided between the roller clip 12 and the M clamp 13.

In addition, while the roller clip 12 is provided downstream of a section (the first tube 50) of the tube 11 to which the infusion pump device 40 is mounted in the above embodiment, the roller clip 12 may be provided in the section of the tube 11 to which the infusion pump device 40 is mounted. Also in this case, the M clamp 13 is provided upstream of the section of the tube 11 to which the infusion pump device 40 is mounted.

The infusion set 1 may include, in advance, the first upstream tube 14, the second upstream tube 15, the first clamp 16, and the second clamp 17 as in the above embodiment or, instead of including them, a set of the first upstream tube 14, the second upstream tube 15, the first clamp 16, and the second clamp 17 which is prepared separately may be used in combination with the infusion set.

Figure 7:
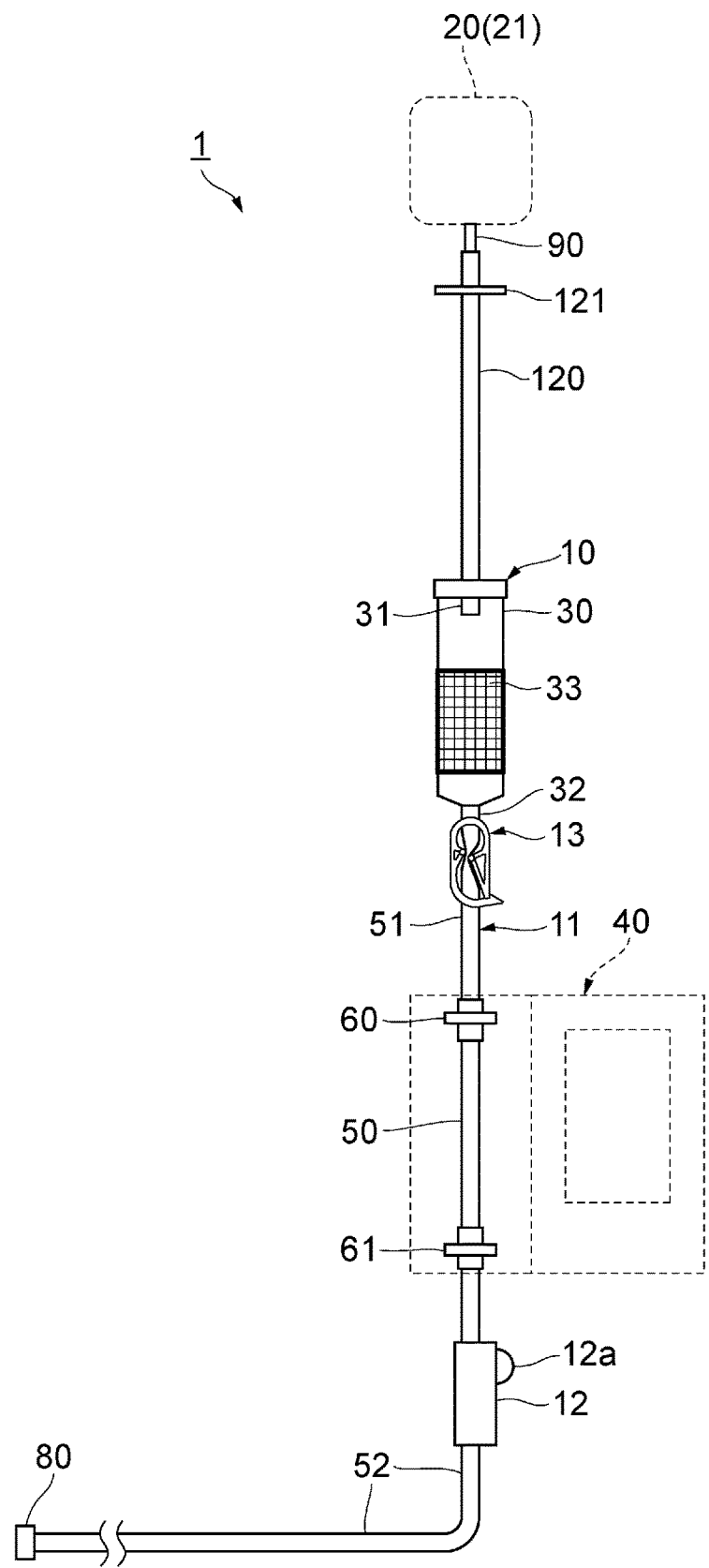
FIG. 7 is a schematic view showing an example of the structure of the infusion set of another embodiment in the case where one upstream tube is provided.
Figure 8:
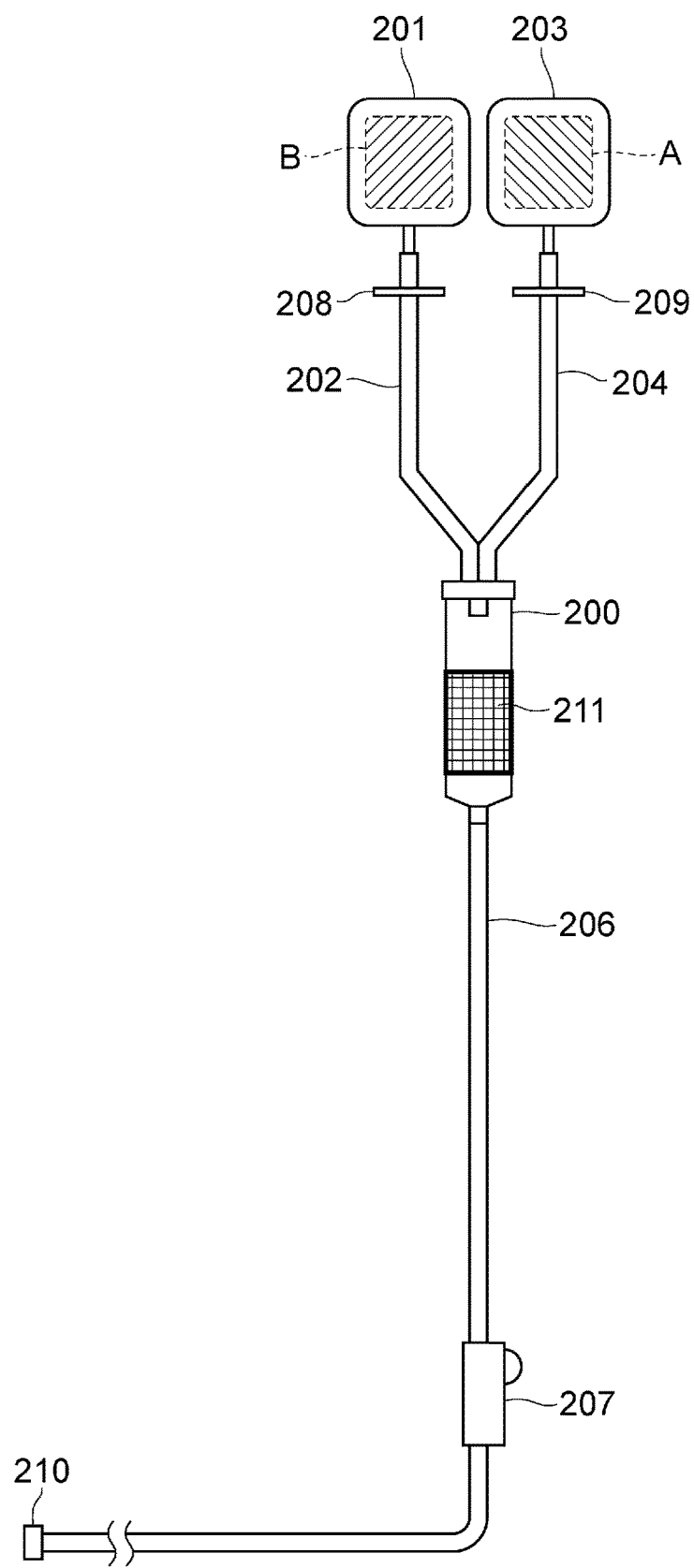
FIG. 8 is a schematic view showing the structure of a conventional infusion set.

While the infusion set 1 includes two sets of the upstream tube and the clamp, the infusion set 1 may also include one upstream tube 120 which is connected to the inlet of the drip chamber 10 as shown in FIG. 7 and can be connected to the liquid bag 20 (21), and a clamp 121 which is provided in the upstream tube 120. In such a case, the upstream tube 120 may be connected to the second bag 21 serving as the saline bag first and, after the second bag 21 is replaced with the first bag 20, the upstream tube 120 may be then connected to the first bag 20 serving as the blood bag. Note that the structures of the other portions of the infusion set 1 of the present aspect may be similar to, e.g., those in the above embodiment.

In the above embodiment, the flow rate adjustment part is not limited to the roller clip, and may also be, e.g., a one-touch clip or a slide clip. In the infusion set 1, the tube 11 may be mounted to the infusion pump device 40 or may not be mounted to the infusion pump device 40. The infusion set 1 can be applied not only to the case where blood transfusion is performed but also to the case where a drug or the like is infused. The drug solution supplied to the drip chamber 10 described in the above embodiment is not limited to the saline A.

According to the present invention, it is possible to provide the infusion set capable of significantly reducing a period of time required for the work of the worker during infusion.

What is claimed is:

1. An infusion method using an infusion set, wherein the infusion set includes:
    a drip chamber;
    a first upstream tube which connects a blood bag and an inlet of the drip chamber;
    a second upstream tube which connects a saline bag and the inlet of the drip chamber;
    a tube which is connected to an outlet of the drip chamber;
    a clip which is provided in the tube;
    an M clamp which is provided between the drip chamber and the clip in the tube;
    a first upstream clamp which is provided in the first upstream tube; and
    a second upstream clamp which is provided in the second upstream tube,
    the infusion method comprising:
    a first step of, in a state in which the M clamp and the first upstream clamp are closed, opening the second upstream clamp to supply saline in the saline bag through the second upstream tube to the drip chamber while preventing the saline in the drip chamber from flowing into the tube by the closed M clamp;
    a second step of, in a state in which the M clamp and the second upstream clamp are closed, opening the first upstream clamp to supply blood in the blood bag through the first upstream tube to the drip chamber and produce diluted blood with the saline in the drip chamber while preventing the diluted blood in the drip chamber from flowing into the tube by the closed M clamp; and
    a third step of, in a state in which the second upstream clamp is closed, opening the M clamp, the first upstream clamp and the clip to supply the diluted blood in the drip chamber through the tube to a tip end of the tube and thereby remove a gas in the tube.

2. The infusion method according to claim 1, further comprising:
    a fourth step of mounting a section of the tube between the M clamp and the clip to an infusion pump device; and
    a fifth step of operating the infusion pump device to perform infusion.

3. The infusion method according to claim 1, wherein the M clamp clamps the tube at a position within 10 cm from the outlet of the drip chamber in the tube.

4. The infusion method according to claim 1, wherein the first step includes supplying the saline to the drip chamber by increasing and decreasing an internal capacity of the drip chamber.

5. The infusion method according to claim 1, wherein the second step includes supplying the blood to the drip chamber by increasing and decreasing an internal capacity of the drip chamber.

\* \* \* \* \*